United States Patent
Vivenzio et al.

(10) Patent No.: US 9,314,149 B2
(45) Date of Patent: Apr. 19, 2016

(54) ILLUMINATION DEVICE, SYSTEM, AND METHOD OF USE

(71) Applicant: Welch Allyn, Inc., Skaneateles Falls, NY (US)

(72) Inventors: Robert L. Vivenzio, Skaneateles Falls, NY (US); Raymond A. Lia, Skaneateles Falls, NY (US); Michael T. McMahon, Skaneateles Falls, NY (US); Jon R. Salvati, Skaneateles Falls, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 243 days.

(21) Appl. No.: 13/839,205

(22) Filed: Mar. 15, 2013

(65) Prior Publication Data

US 2014/0275790 A1 Sep. 18, 2014

(51) Int. Cl.
*A61B 1/267* (2006.01)
*A61B 1/06* (2006.01)
*A61B 1/303* (2006.01)
*A61B 1/32* (2006.01)

(52) U.S. Cl.
CPC . *A61B 1/06* (2013.01); *A61B 1/303* (2013.01); *A61B 1/32* (2013.01)

(58) Field of Classification Search
CPC ...... A61B 1/06; A61B 1/0661; A61B 1/0669; A61B 1/0676; A61B 1/0684; A61B 1/0692
USPC .................................................. 600/184–246
See application file for complete search history.

(56) References Cited

U.S. PATENT DOCUMENTS

| | | | |
|---|---|---|---|
| 3,789,835 | A | 2/1974 | Whitman |
| 4,067,323 | A | 1/1978 | Troutner et al. |
| D343,453 | S | 1/1994 | Noda |
| D367,087 | S | 2/1996 | Mathews |
| D375,372 | S | 11/1996 | Allen |
| 6,004,265 | A | 12/1999 | Hsu et al. |
| D425,226 | S | 5/2000 | Galli |
| D445,928 | S | 7/2001 | Sharrah et al. |
| D446,324 | S | 8/2001 | Lynch et al. |
| D446,325 | S | 8/2001 | Guerrieri |
| 6,379,296 | B1 | 4/2002 | Baggett |
| D457,670 | S | 5/2002 | Allen |
| D482,469 | S | 11/2003 | Guerrieri |
| D492,050 | S | 6/2004 | Chung |
| D498,553 | S | 11/2004 | Lee |

(Continued)

OTHER PUBLICATIONS

Design U.S. Appl. No. 29/434,856, filed Oct. 17, 2012; in re: Vivenzio et al., entitled *Illuminator for a Medical Device or the Like*.

(Continued)

*Primary Examiner* — Ellen C Hammond
*Assistant Examiner* — Christina Negrellirodriguez

(57) ABSTRACT

An illumination device for a speculum may include a first housing part and a second housing part that define a cavity therein. The illumination device may further include a pull tab configured to move from a first position to a second position. When the pull tab moves from the first position to the second position, the pull tab may be disposed so as to allow an electric circuit to be complete so as to provide illumination from an illumination source. When the pull tab is disposed in the first position, the pull tab may be positioned to interrupt the electric circuit such that the illumination device is in an unilluminated state.

21 Claims, 14 Drawing Sheets

(56) References Cited

U.S. PATENT DOCUMENTS

| | | | |
|---|---|---|---|
| D498,864 S | 11/2004 | Lee | |
| D501,266 S | 1/2005 | Harris, Jr. et al. | |
| D507,368 S | 7/2005 | Waters | |
| D507,369 S | 7/2005 | Waters | |
| D507,671 S | 7/2005 | Rice | |
| D513,084 S | 12/2005 | Parker et al. | |
| 7,029,439 B2* | 4/2006 | Roberts | A61B 1/227 600/178 |
| D565,216 S | 3/2008 | Markell | |
| D576,323 S | 9/2008 | Cienfuegos | |
| D577,143 S | 9/2008 | Lu | |
| D581,566 S | 11/2008 | Slawson et al. | |
| D593,693 S | 6/2009 | Adamany et al. | |
| D594,148 S | 6/2009 | Heselden | |
| D598,593 S | 8/2009 | Kingston et al. | |
| D627,092 S | 11/2010 | Puglisi | |
| 7,841,751 B2 | 11/2010 | Mulani | |
| 7,909,759 B2* | 3/2011 | Pecherer | 600/193 |
| D642,310 S | 7/2011 | Idelson | |
| D656,644 S | 3/2012 | Lee | |
| 8,142,352 B2 | 3/2012 | Vivenzio et al. | |
| 8,152,330 B2 | 4/2012 | Waters | |
| 8,157,728 B2 | 4/2012 | Danna et al. | |
| D659,845 S | 5/2012 | Lytle | |
| D676,992 S | 2/2013 | Trude | |
| 8,409,082 B2 | 4/2013 | Irion et al. | |
| D683,489 S | 5/2013 | Lee | |
| D690,043 S | 9/2013 | Sun | |
| RE44,806 E * | 3/2014 | Roberts et al. | 315/205 |
| 8,740,780 B2 | 6/2014 | Honda et al. | |
| D710,500 S | 8/2014 | Roeloffs | |
| 8,808,175 B2 | 8/2014 | Deitch et al. | |
| D712,561 S | 9/2014 | Hagenauer | |
| 9,173,648 B2 | 11/2015 | Vayser et al. | |
| 2006/0007669 A1 | 1/2006 | Blackburn | |
| 2006/0029901 A1 | 2/2006 | Rose et al. | |
| 2008/0045801 A1* | 2/2008 | Shalman | A61B 1/267 600/193 |
| 2008/0228038 A1 | 9/2008 | McMahon et al. | |
| 2009/0076334 A1 | 3/2009 | Chen | |
| 2009/0312610 A1* | 12/2009 | Buchok et al. | 600/205 |
| 2012/0108907 A1 | 5/2012 | Fitipaldi et al. | |
| 2014/0293590 A1 | 10/2014 | Pathy | |

OTHER PUBLICATIONS

Design U.S. Appl. No. 29/434,858, filed Oct. 17, 2012; in re: Vivenzio et al., entitled *Illuminator for a Medical Device or the Like*.

U.S. Appl. No. 13/839,205, filed Mar. 15, 2013; in re: Vivenzio et al., entitled *Illumination Device, System, and Method of Use*.

Disposable Vaginal Speculum With Cordless LED Source, MedGyn Products, Inc. [online] [retrieved May 1, 2014]. Retrieved from the Internet: <URL: http://medgyn.com/?wpsc-product=disposable-speculum-cordless-led>. (dated 2014) 2 pages.

ER-SPEC Single-use Vaginal Specula with Built-In LED-Use Light Source, OBP Medical Inc. . [online] [retrieved May 1, 2014]. Retrieved from the Internet: <URL: https://obpmedical.com/product/er-spec/>. (dated 2014) 3 pages.

ER-SPECS Single-Use Vaginal Speculum with Built-In Light Source, OBP Medical Inc. (brochure) (dated Apr. 16, 2014) 2 pages.

ER-SPEC, Tired of Search for a Light Source?, OBP Medical Inc. (Rep Brochure) (Feb. 2012 revision) 2 pages.

ER-SPEC Presentation, OBP Medical (dated Apr. 16, 2014), 12 pages.

ER-SPEC® User Manual, OBP Medical (dated Jun. 27, 2013), 10 pages.

Restriction Requirement from U.S. Appl. No. 29/495,181 dated Aug. 14, 2015.

Office Action from U.S. Appl. No. 29/434,858 dated Jul. 24, 2015.

Notice of Allowance from U.S. Appl. No. 29/434,856 dated Jun. 17, 2015.

Office Action from U.S. Appl. No. 29/434,858 dated Dec. 4, 2015.

Notice of Allowance from U.S. Appl. No. 29/495,181 dated Nov. 20, 2015.

* cited by examiner

ILLUMINATION DEVICE, SYSTEM, AND METHOD OF USE

TECHNICAL FIELD AND BACKGROUND OF THE INVENTION

Embodiments of the present invention generally relate to an illumination device for a speculum and associated methods for using a speculum with an illumination device.

During a physical exam, speculums, probes, or other physical-assessment devices (e.g. otoscopes, ophthalmoscopes, laryngoscopes, colposcopes, etc.) may be used to provide a user with a better view of a patient for an examination. Current methods of using such devices may not provide users with sufficient illumination. Further, illumination devices used in conjunction with a speculum, probe, or physical-assessment device may be difficult to handle during an examination of a patient. Accordingly, there is a need for illumination devices that facilitate the use of speculums, probes, and physical-assessment devices in a cost efficient and practical manner.

BRIEF SUMMARY

Various embodiments of the present invention are directed to an illumination device for a speculum and associated methods for using a speculum with an illumination device. It is, however, contemplated that the disclosed illumination devices may be adapted for use in other probes or physical-assessment devices.

In some embodiments, an illumination device may include a housing that comprises a first housing part and a second housing part. The first housing part and the second housing part may define a cavity therebetween. In some embodiments, the illumination device may include an illumination source that is disposed within the housing. The illumination device may further include at least one battery disposed within the cavity of the housing configured to energize an electric circuit for providing power to the illumination source. In some embodiments, the illumination device may include a pull tab partially disposed within the cavity of the housing and configured to be moved between a first and second position. In the first position, the pull tab may be positioned to interrupt the electric circuit such that the illumination device is in an unilluminated state. In the second position, the pull tab is positioned to allow the electric circuit to be complete such that the illumination device is in an illuminated state.

In some embodiments, the illumination device may comprise a plurality of batteries disposed within the cavity. When the pull tab is disposed in the first position, the pull tab may be positioned between at least two adjacent batteries to preclude electrical contact between the two batteries. When the pull tab is positioned in the second position, the pull tab is positioned to allow electrical contact between the two batteries. In some embodiments, the illumination device may include a current regulator device disposed within the housing. The current regulator device may be configured to regulate the power to the illumination source. In some embodiments, the current regulator device may comprise at least one resistor.

In some embodiments, the illumination device may include a pull tab that defines a pull tab slot therethrough. The pull tab slot may be configured to retain the pull tab at least partially in the cavity when the pull tab is positioned in the second position. In some embodiments, the illumination device may include a housing that further defines a pull tab stop, the pull tab stop being configured to engage the pull tab through the pull tab slot. An inner surface of the housing may define the pull tab stop. According to some embodiments, the pull tab stop extends along an axis orthogonal to a longitudinal axis of the pull tab. In another embodiment, the pull tab may be configured to move in a direction substantially parallel to the longitudinal axis of the illumination device.

According to some embodiments, the illumination device may include a housing having an outer surface that defines a plurality of raised grooves configured to mate with reciprocal channels of a speculum cavity so as to facilitate alignment of the illumination device therein. In some embodiments, the housing may further define a first portion, a second portion and a third portion, wherein an illumination source is disposed proximate the first portion, and wherein a pull tab is disposed proximate the third portion. In some embodiments, the second portion may define a shape that substantially corresponds to the shape of a battery.

In some embodiments, the illumination device may further include at least one securing member configured to maintain engagement of a first housing part with a second housing part. The at least one securing member may be a wire clip member configured to bias the housing parts together. In another embodiment, the at least one securing member may be a ring comprising elastomeric material that is configured to bias the housing parts together.

Some embodiments may provide a system for use during an examination of a patient that includes a speculum comprising a handle defining a handle cavity therein, at least two blades, wherein a second blade is coupled to the handle, and a light pipe configured to illuminate the speculum, wherein the light pipe extends from a proximal end disposed proximate the handle to a distal end disposed proximate the second blade. In some embodiments, the system may further include an illumination device comprising a housing that includes a first housing part and a second housing part. The first housing part and the second housing part may define a housing cavity therebetween. In some embodiments, the illumination device may further include an illumination source disposed within the housing, at least one battery disposed within the housing cavity of the housing configured to energize an electric circuit for providing power to the illumination source, and a pull tab partially disposed within the housing cavity and configured to be moved between a first and second position. When the pull tab is disposed in the first position, the pull tab may be positioned to interrupt the electric circuit such that the illumination device is in an unilluminated state, and when the pull tab is disposed in the second position, the pull tab may be positioned to allow the electric circuit to be complete such that the illumination device is in an illuminated state.

In some embodiments, the system may include a speculum wherein the handle cavity is configured to receive the illumination device therein, and wherein the illumination source is configured to illuminate the proximal end of the light pipe thereby illuminating the speculum. In some embodiments, the system may include an illumination device that includes a plurality of batteries disposed within the housing cavity. When the pull tab is disposed in the first position, the pull tab is disposed between at least two adjacent batteries to preclude electrical contact between the two batteries. In some embodiments, when the pull tab is disposed in the second position, the pull tab is positioned to allow electrical contact between the two batteries.

The system may further include a pull tab that defines a pull tab slot therethrough, wherein the pull tab slot is configured to retain the pull tab at least partially within the housing cavity in the second position. In some embodiments, the system may include an illumination device that comprises a housing that further defines a pull tab stop, the pull tab stop being configured to engage the pull tab through the pull tab slot. In some embodiments, the inner surface of the housing may define the pull tab slot. According to some embodiments, the illumination device may be configured to be removed from a handle or speculum cavity when tension is applied to the pull tab after the pull tab stop is engaged with an end of the pull tab slot. In some embodiments, the pull tab stop may extend along an axis that is orthogonal to a longitudinal axis of the pull tab. In some embodiments, the pull tab may be configured to move in a direction that is substantially parallel to a longitudinal axis of the illumination device and/or the speculum cavity.

Other systems, methods, and features will be, or will become, apparent to one with skill in the art upon examination of the following figures and detailed description. It is intended that all such additional systems, methods, and features be included within this description and be within the scope of the disclosure.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. The terms top, bottom, side, up, down, upwards, downwards, vertical, horizontal, and the like, to the extent used herein, do not imply a required limitation in all embodiments of the present invention, but rather are used herein to help describe relative direction or orientation in the example embodiments illustrated in the figures.

Various embodiments of the present invention generally provide for a system configured to provide illumination for a speculum and associated methods of illuminating a speculum. For example, the system may include a speculum and an illumination device configured to illuminate the speculum and/or a patient during a physical examination. Specifically, a speculum may be configured to receive an illumination device in a speculum cavity. The speculum cavity may be configured to receive the illumination device and may be further configured to illuminate the speculum and/or a patient during a physical examination via a light pipe that extends from the speculum cavity to a speculum blade. In addition, the illumination device may be configured to provide for easy illumination with a pull tab that is configured to switch the illumination device between an illuminated state and an unilluminated state. Further, the system may advantageously provide for easy replacement of an illumination device by providing an illumination device with a pull tab configured to allow for the removal of the illumination device from a speculum cavity.

Figure 1:
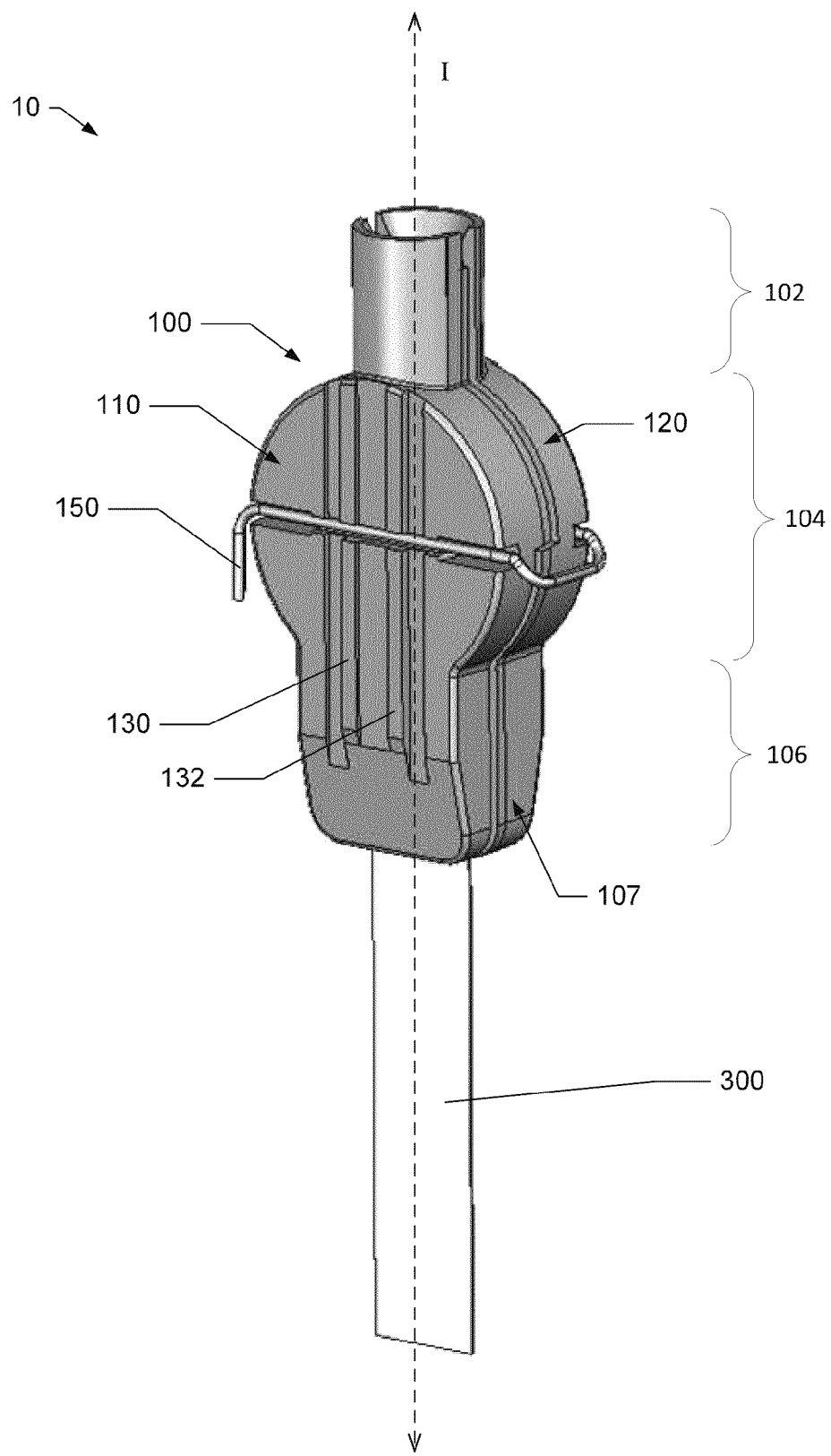
FIG. 1 illustrates a perspective view of an illumination device according to an example embodiment.
Figure 11:
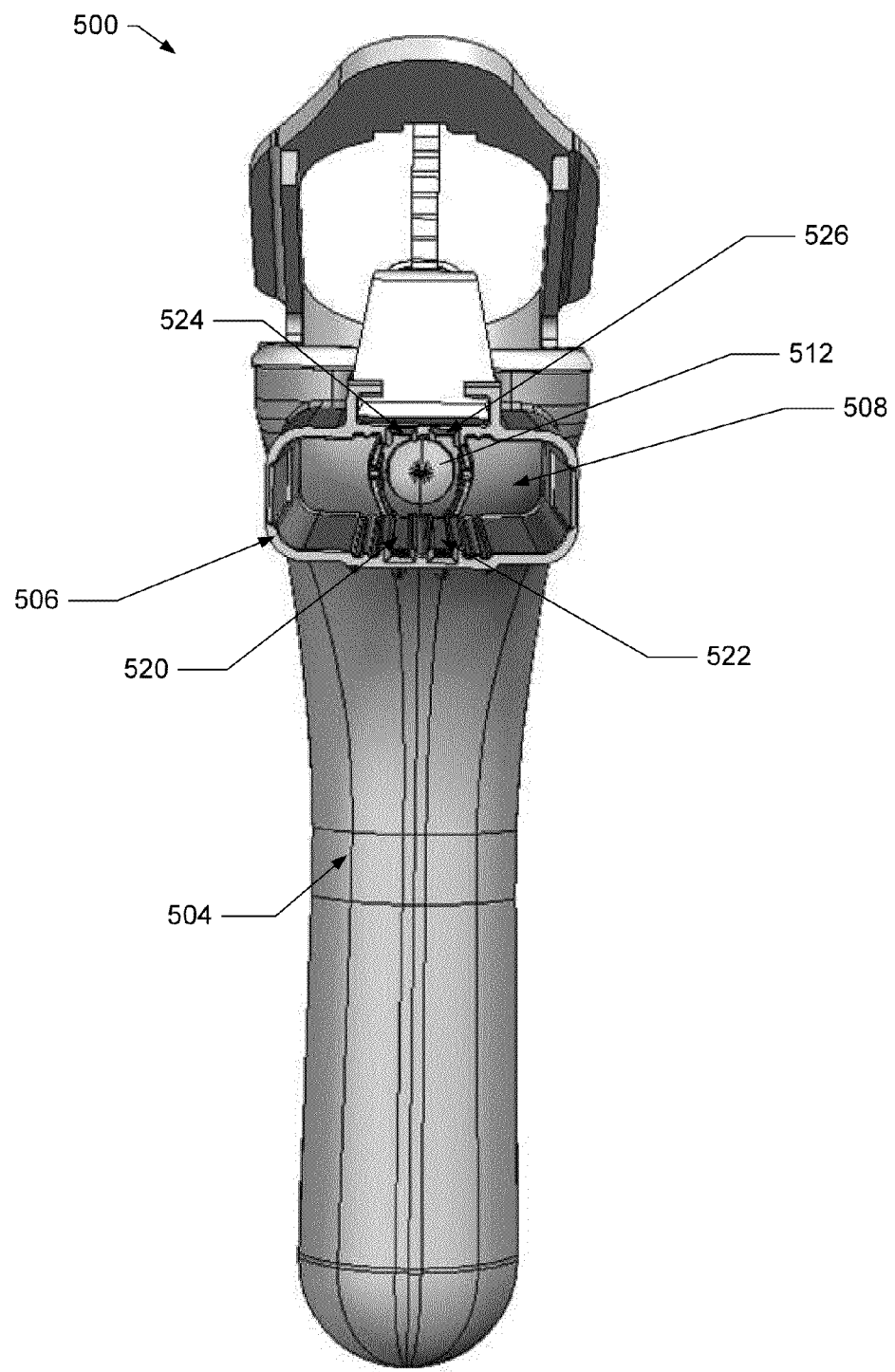
FIG. 11 illustrates a bottom view of a speculum according to an example embodiment.
Figure 12:
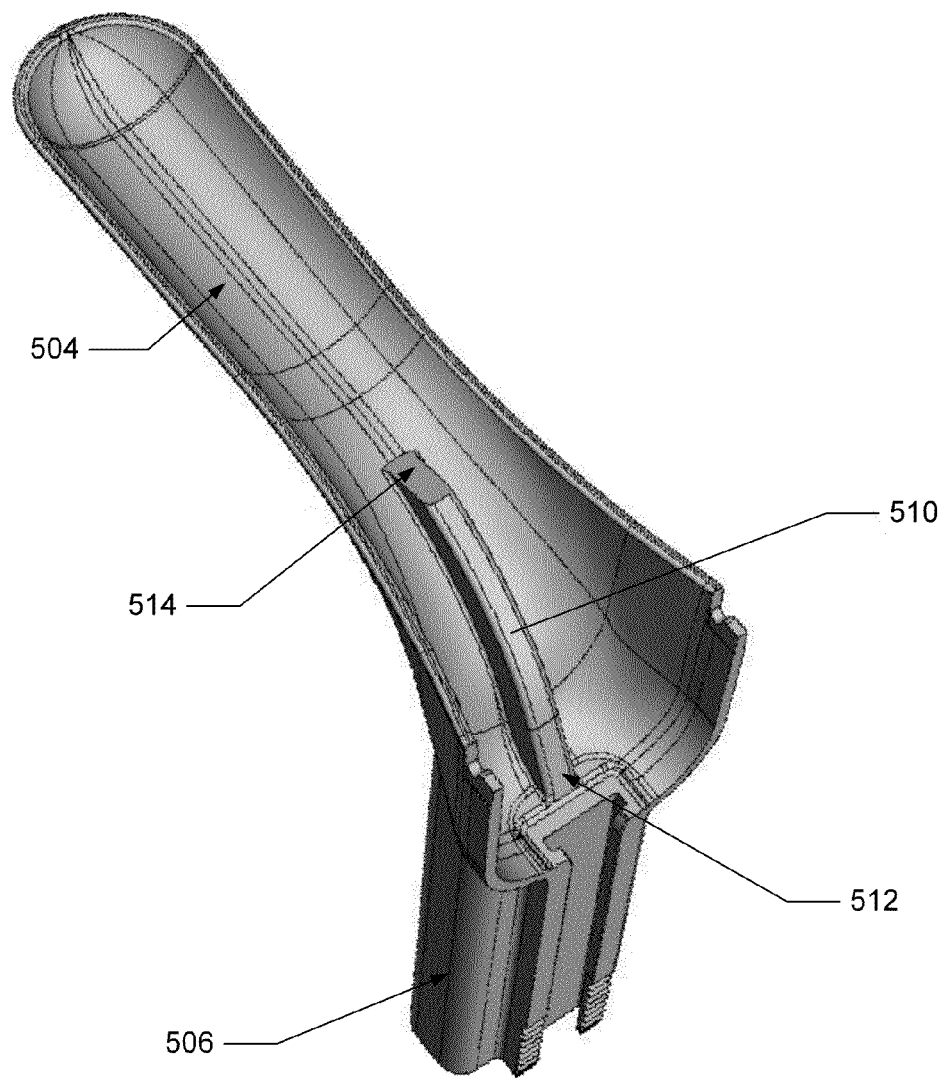
FIG. 12 illustrates a perspective view of a bottom blade of a speculum according to an example embodiment.

In this regard, FIG. 1 illustrates an illumination device 10 for a system configured to illuminate a speculum and/or a patient during a physical exam according to one embodiment of the present invention. Specifically, the illumination device 10 may comprise a housing 100 configured to be received within a speculum cavity 508, as shown in FIG. 11. In some embodiments, the illumination device 10 may comprise a housing 100 that includes a first housing part 110 and a second housing part 120, as shown in FIG. 1. The illumination device 10 may include a securing member 150 configured to couple the first housing part 110 and second housing part 120 to one another. The illumination device 10 may also include a pull tab 300 that is partially disposed within the housing 100. As such, embodiments herein may provide an illumination device for a system configured to illuminate a speculum and/or or a patient that may be modular in design. Accordingly, replacement or repair of the illumination device is facilitated by providing a housing that provides accessible means to various illumination device components. Further, some embodiments may provide a housing for an illumination device that may be discarded after use, such as in an instance where the illumination device has become contaminated with a biological agent and/or is designed to be a single-use component.

According to some embodiments, the housing 100 may comprise a single housing part that is formed from an elastomeric material. In some embodiments, a single housing may be shaped to form a clam shell design such that a hinged portion of the housing may provide access to a housing cavity defined therein. Further, in some embodiments, the hinged portion may be defined by a first portion of the housing such that one part of a second and third portion of the housing may be moved away from and/or toward a second part of the second and third portion of the housing. In another embodiment, the second portion may define the hinged portion along a longitudinal axis, such that one part of a first, second and third portion of the housing may be moved away from and/or toward a second part of the first, second and third portion of the housing. As such, embodiments of the present invention may advantageously provide for facilitating the assembly of the illumination system. Specifically, the illumination device may be configured to be secured within a speculum cavity via an interference fit without the need for a securing member in some embodiments.

Figure 4:
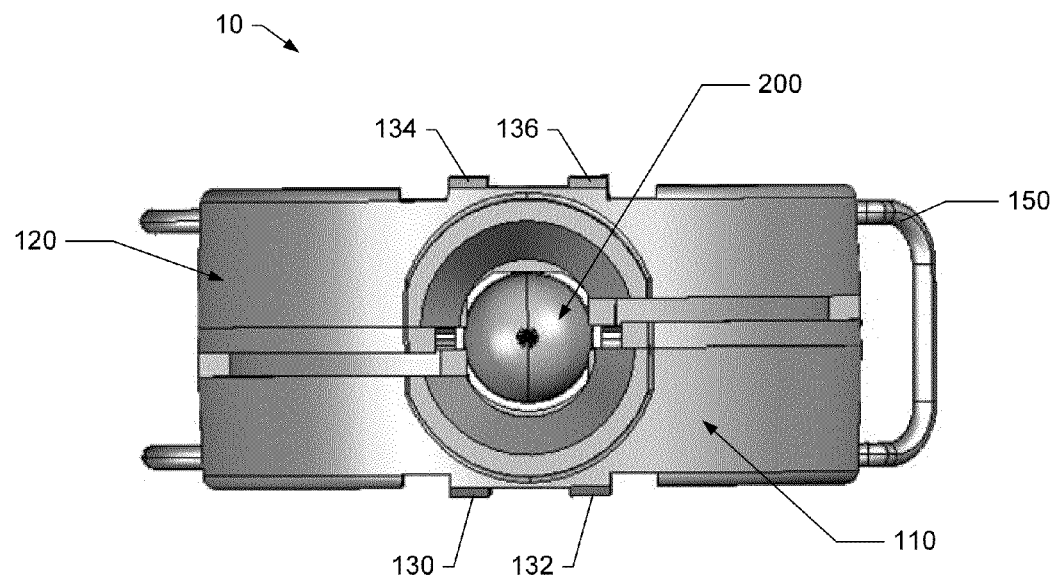
FIG. 4 illustrates a top view of a housing of an illumination device according to an example embodiment.
Figure 5:
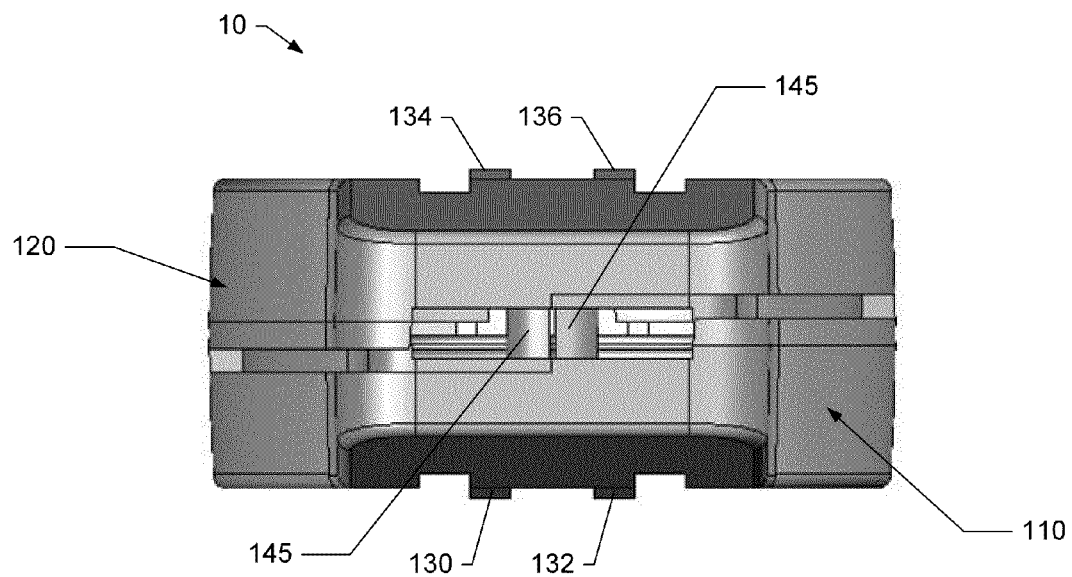
FIG. 5 illustrates a bottom view of a housing of an illumination device with various parts removed for clarity according to an example embodiment.

According to one embodiment, the housing 100 may define a first portion 102, a second portion 104, and a third portion 106, as shown in FIG. 1. Specifically, the first portion 102, second portion 104, and third portion 106 may be different regions of the housing 100. The first portion 102 may be a top region of the housing 100 near an illumination source 200, the second portion 104 may be a middle region of the housing, and the third portion 106 may be a bottom portion of the housing. In addition, as shown in FIGS. 4 and 5, the housing 100 may further define a plurality of raised grooves 130, 132, 134, 136. The plurality of raised grooves may be configured to mate with reciprocal channels 520, 522, 524, 526 of a speculum cavity 508, as shown in FIG. 11. Although FIG. 4 and FIG. 11 illustrate a housing defining four grooves and a speculum cavity defining four reciprocal channels, one of ordinary skill in the art in view of this disclosure may appreciate that the housing and speculum cavity may define any number of grooves and reciprocal channels. In some embodiments, the plurality of raised grooves may extend longitudinally from the third portion 106 of the housing to at least the second portion 104 of the housing, as shown in FIG. 1. In some embodiments, the plurality of raised grooves may extend from the third portion 106 of the housing to the first portion 102 of the housing. As such, embodiments of the present invention may advantageously provide for an illumination device that is securely disposed within a speculum cavity. In addition, the plurality of raised grooves of the illumination device housing and the reciprocal channels of the speculum cavity may be configured to minimize lateral movement of the illumination device within the speculum cavity when the illumination device is inserted therein. Further, the plurality of raised grooves and the reciprocal channels may be configured to advantageously provide for the alignment of an illumination source of the illumination device and a light pipe of the speculum so as to maximize the amount of illumination along a direction angled away from the longitudinal axis of the illumination device, as described in greater detail below.

Figure 2A:
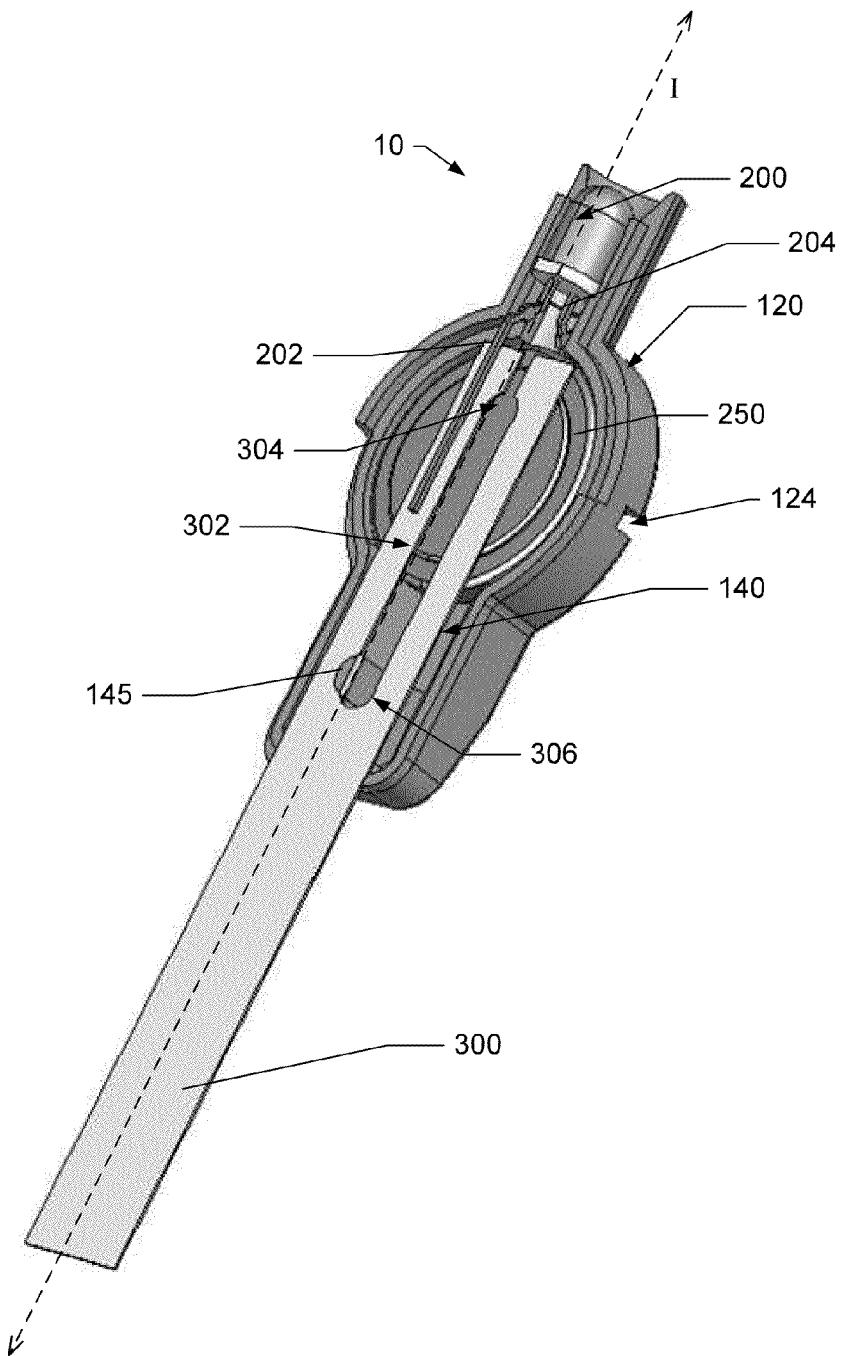
FIG. 2A illustrates a perspective view of an illumination device with various parts removed for clarity according to an example embodiment.
Figure 2B:
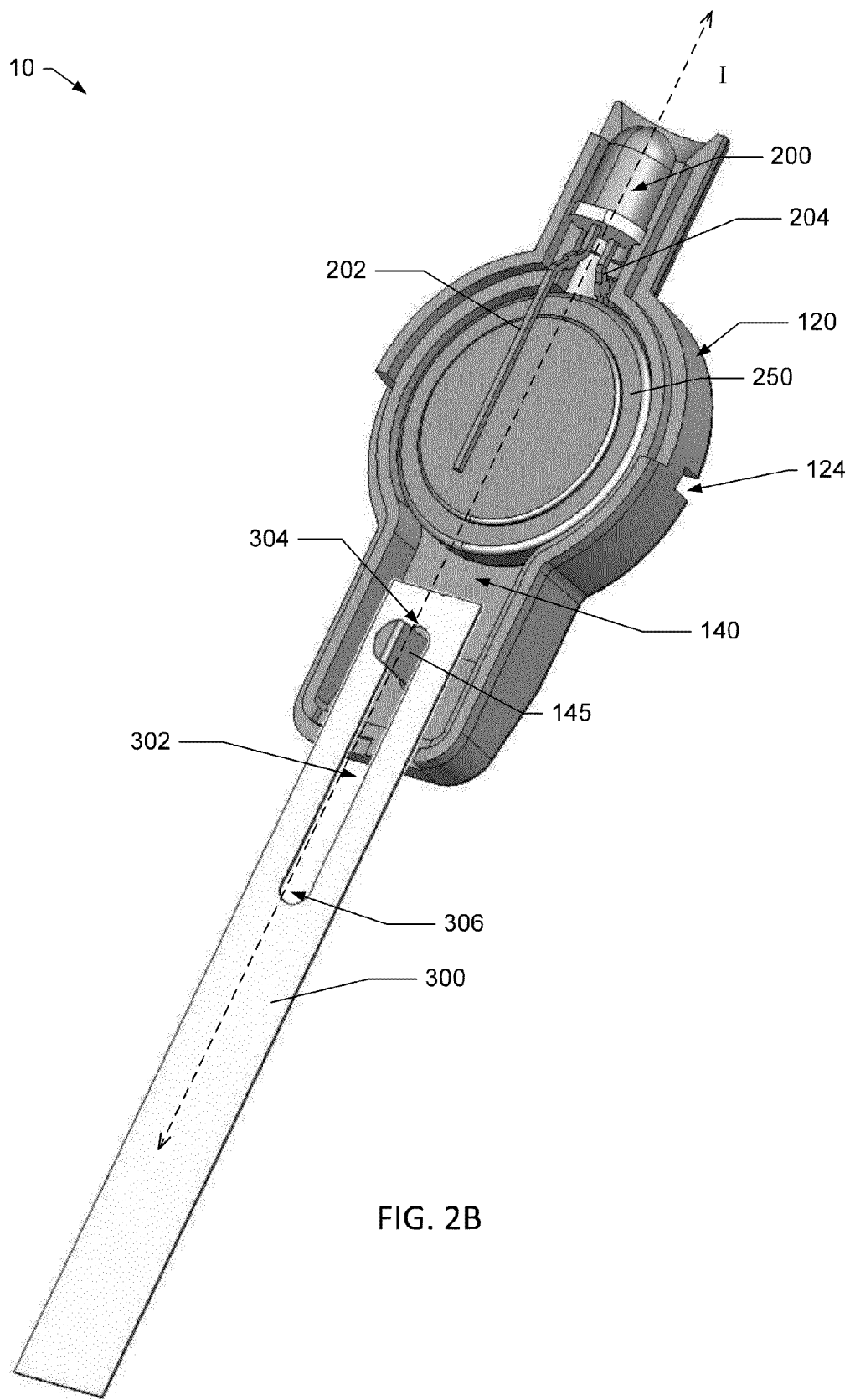
FIG. 2B illustrates a perspective view of an illumination device with various parts removed for clarity according to an example embodiment.
Figure 3:
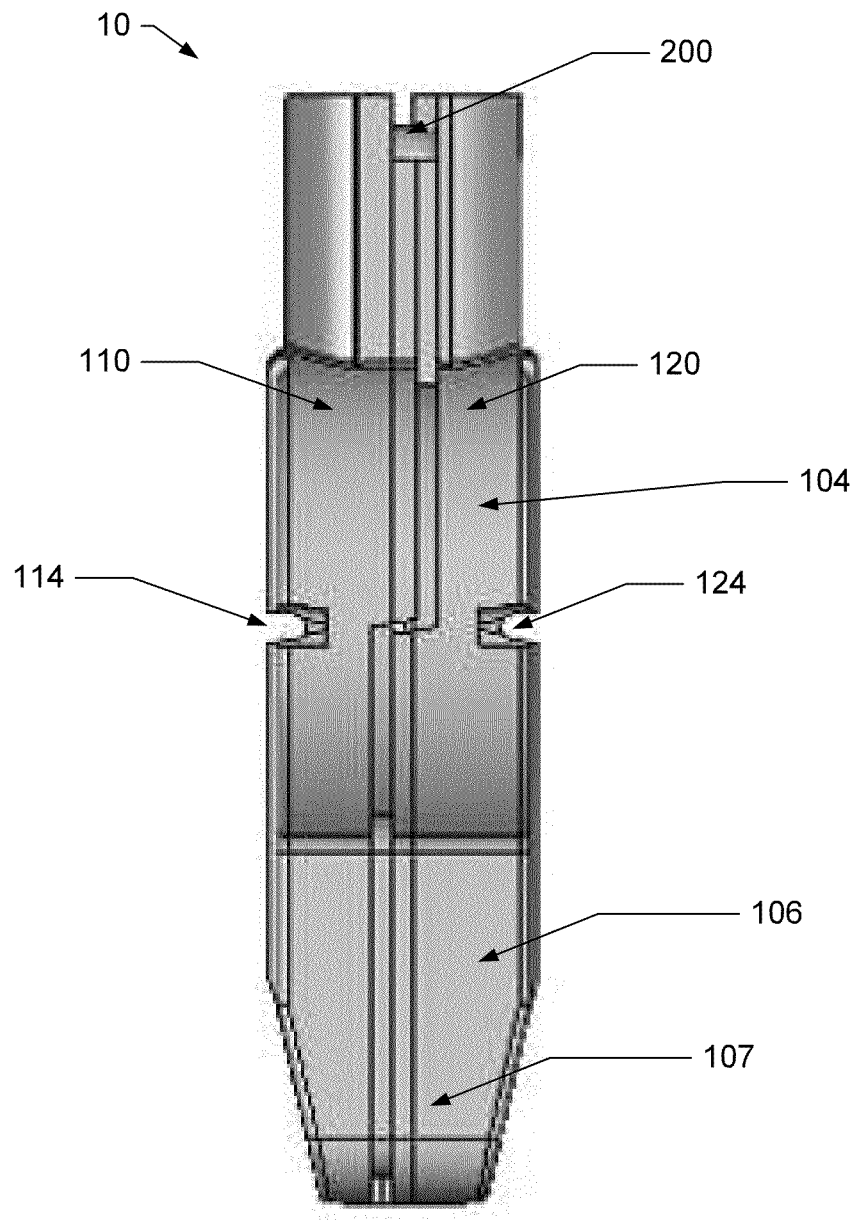
FIG. 3 illustrates a side view of a housing of an illumination device with various parts removed for clarity according to an example embodiment.

As noted above, the housing 100 may comprise at least a first and second housing part 110, 120. As shown in FIGS. 2A, 2B and 3, the housing 100 may also define a plurality of channels 114, 124 configured to receive a securing member 150 therein so as to bias the first housing part 110 in engagement with the second housing part 120. Although FIG. 1 illustrates a single securing member 150 configured to bias the first and second housing parts 110, 120 in engagement with one another, one of skill in the art may appreciate that the housing may include any number of securing members and a corresponding number of channels configured to receive the securing members therein. As shown in FIG. 3, the plurality of channels 114, 124 may be defined by the second portion 104 (e.g., the middle portion and/or region) of the housing 100. In some embodiments, the housing may define a plurality of channels in the second portion for a securing member and another plurality of channels in the first portion for a second securing member. According to one embodiment, the first and third portions of the housing may define a plurality of channels configured to receive a securing member respectively therein. As will be appreciated by one of skill in the art, a plurality of channels may be defined by any of the portions of the housing, and the housing may define any number of plurality of channels configured to receive a securing member therein so as to bias the first and second housing parts in engagement with one another.

Figure 8:
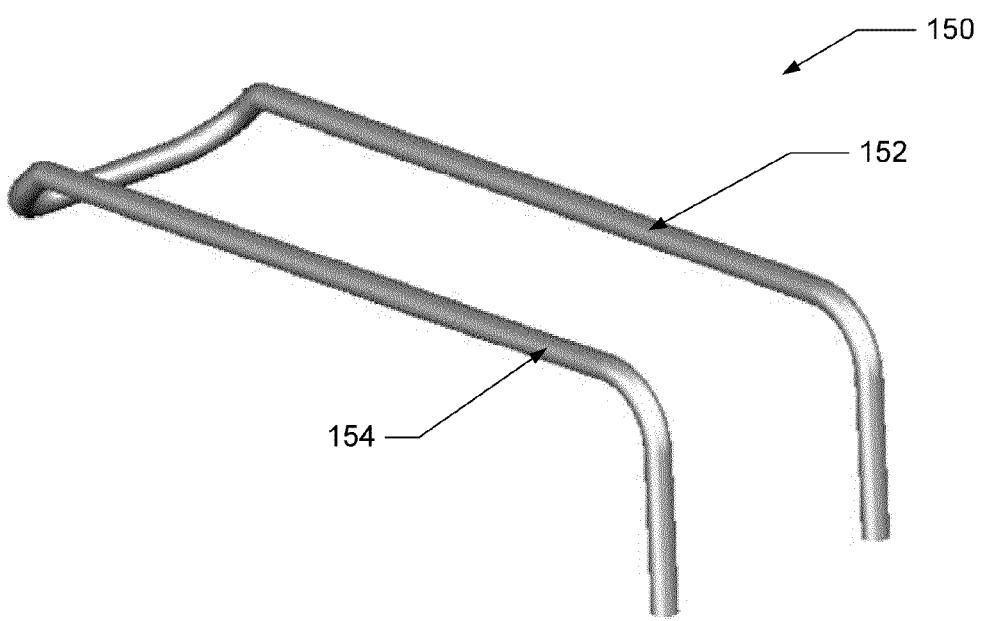
FIG. 8 illustrates a securing member according to an example embodiment.
Figure 9:
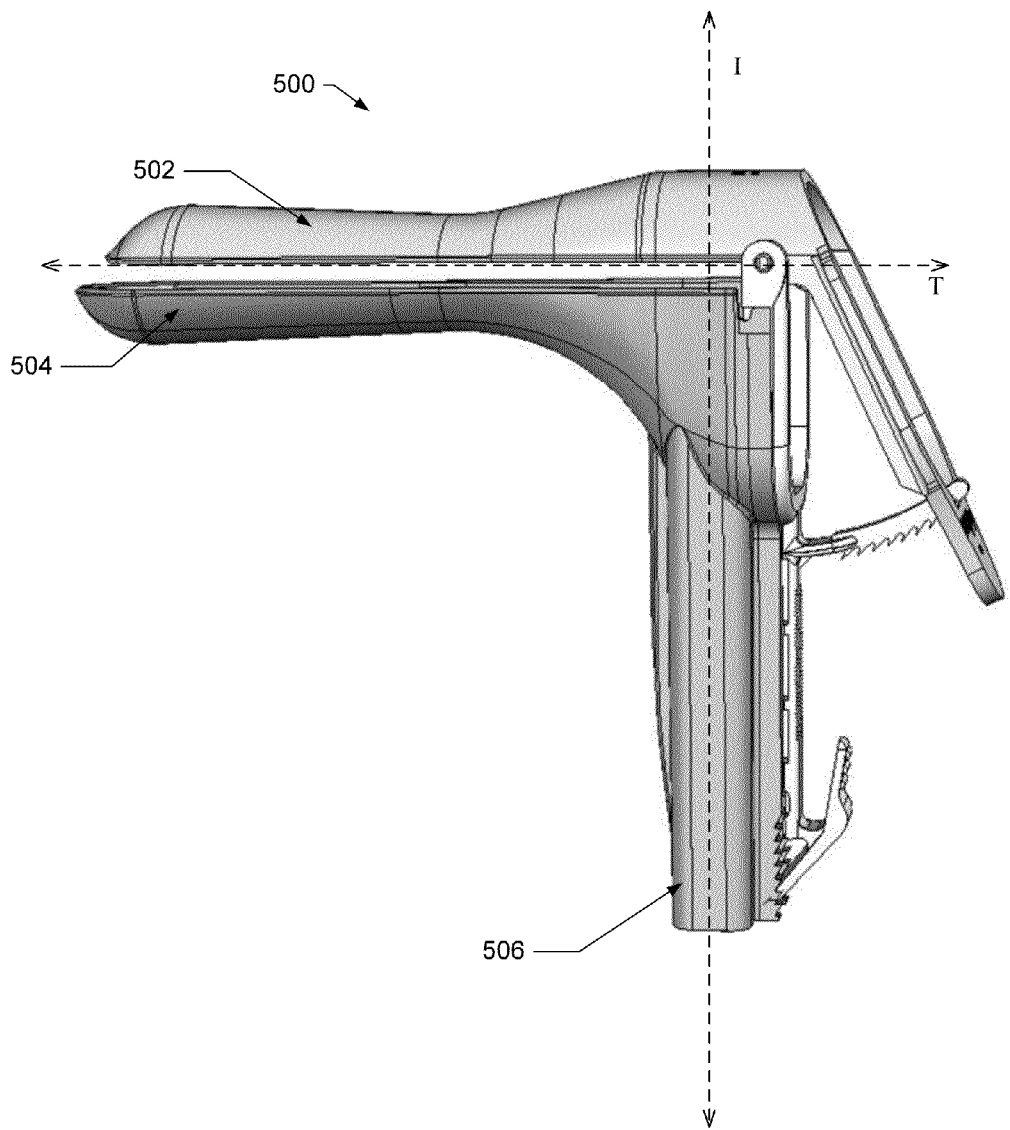
FIG. 9 illustrates a side view of a speculum according to an example embodiment.

In one embodiment, the securing member 150 may be a wire clip configured to bias the first housing part and second housing part to maintain engagement with one another. The wire clip may comprise a spring clip configured to exert a force inwardly between two arms. As shown in FIG. 8, a first arm 152 and a second arm 154 may each be configured to exert a force inwardly (e.g., towards each other). Accordingly, the securing member 150 may be removed from an illumination device by exerting an outward force so as to pull the two arms 152, 154 away from one another. In another embodiment, the securing member may include an elastomeric material such as, for example, an elastomeric o-ring. According to some embodiments, a first securing member may be a wire clip, while a second securing member may include an elastomeric material.

Figure 6:
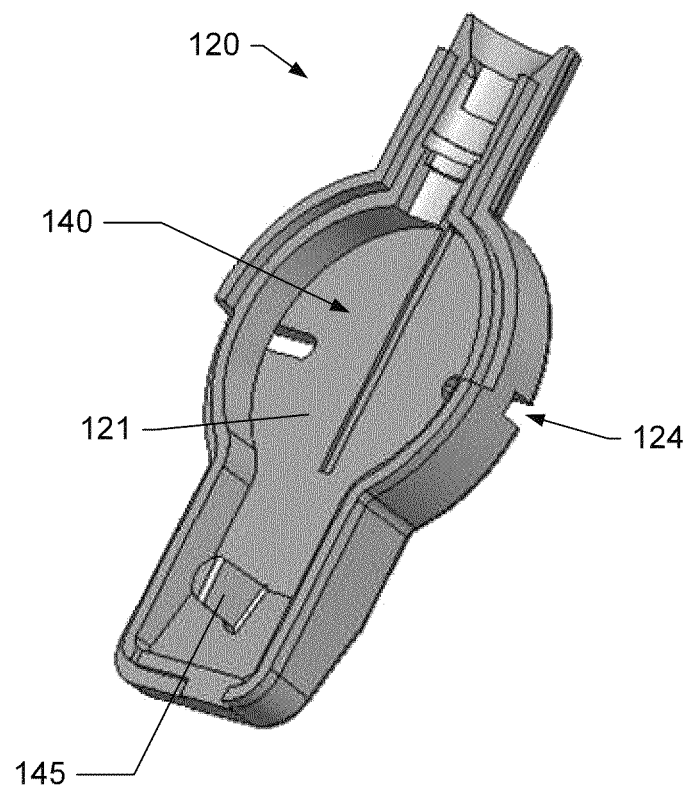
FIG. 6 illustrates one housing part of a housing of an illumination device according to an example embodiment.

The first housing part 110 and the second housing part 120 may define a cavity 140 therebetween. As shown in FIGS. 2A, 2B and 6, the second housing part 120 may define at least a portion of the cavity 140. Accordingly, the first housing part 110 and the second housing part 120 may define and enclose the cavity 140 therebetween when the first and second housing parts are in engagement with one another. In some embodiments, the housing 100 may define a pull tab stop 145. As shown in FIG. 6, for example, the inner surface 121 of the second housing part 120 may define a portion of the pull tab stop 145, which may be an extension of the inner surface or some other protruding feature attached to, coupled with, or integral to the inner surface. The inner surface 111 of the first housing part 110 may define a corresponding portion of the pull tab stop 145, as shown in FIG. 5. For example, according to one embodiment, the second housing part 120 may define approximately half of the pull tab stop 145 (e.g., with a semi-circular shaped portion), while the first housing part 110 may define approximately the other half of the pull tab stop 145 (e.g., with a reciprocally shaped, semi-circular portion).

Referring to FIGS. 2A and 2B, FIGS. 2A and 2B show components of the illumination device 10 with a first housing part 110 and at least one battery removed for ease of explanation. FIGS. 2A and 2B illustrate at least one battery 250 disposed within the housing cavity 140 proximate the second portion 104. In some embodiments, the second portion of the housing may define a shape that substantially corresponds to the shape of the at least one battery, as shown in FIG. 1. In addition, the first portion 102 may define a shape that substantially corresponds to the shape of the illumination source. As shown in FIGS. 1 and 3, in some embodiments, the third portion 106 may include a tapered portion 107 so as to advantageously provide for easier removal from a speculum cavity 508. For example, in an instance where the illumination device 10 is disposed within the speculum cavity 508, the tapered portion 107 may be configured to provide a spacing and/or a gap between the housing 100 of the illumination device and the interior surface of the speculum cavity. As such, a user may be able to grasp the tapered portion 107 of the housing 100 from within the spacing and/or gap defined between the tapered portion and the inner surface of the speculum cavity 508 so as to remove the illumination device 10 from the speculum cavity.

In addition, the illumination device 10 may include an illumination source 200 disposed within the cavity 140 proximate the first portion 102, as shown in FIG. 2. In one embodiment, the illumination source 200 may include a light emitting diode. Further, the illumination source 200 may include a first electrical contact 202 and a second electrical contact 204 that extend from the illumination source. In one embodiment, the first electrical contact 202 and the second electrical contact 204 may extend longitudinally within the housing cavity 140 in a direction from the first portion 102 towards the second portion 104 of the housing. In addition, electrical contacts 202, 204 may be configured to be disposed such that an electrical connection is maintained between each of the respective electrical contacts 202, 204 and at least one battery 250. For example, in FIGS. 2A and 2B, one electrical contact 204 is disposed between the at least one battery 250 and the second housing part 120, while another electrical contact 202 is configured to be disposed between the first housing part (not shown) and at least one other battery (not shown).

In some embodiments, the pull tab 300 may be disposed within the cavity 140. As shown in FIGS. 2A, 2B, 7A and 7B, the pull tab 300 may define a pull tab slot 302 therethrough. The pull tab slot 302 may further define a proximal end 304 and a distal end 306. According to one embodiment, the pull tab 300 may be configured to move between a first position and a second position. For example, in FIG. 2A, the pull tab 300 is shown disposed proximate the first position, whereas in FIG. 2B, the pull tab shown is disposed proximate the second position. In the first position, a distal end 306 of the pull tab slot 302 may be disposed proximate the pull tab stop 145, as shown in FIG. 2A. Accordingly, in the first position, the pull tab 300 may be positioned to interrupt an electrical circuit, such that the illumination device 10 is in an unilluminated state. For example, in the first position, the pull tab 300 may be positioned between two batteries (e.g., the battery 250 and another battery, not shown) such that the two batteries are prohibited from contacting one another, thereby interrupting the electrical circuit that would otherwise be formed between the two batteries and the illumination source 200 via the electrical contacts 202, 204. In another embodiment, the pull tab 300 may be positioned in the first position such that the pull tab is disposed between at least one battery 250 and a portion of the electrical circuit, such as an electrical contact of the illumination source, thereby interrupting the electrical circuit such that the illumination device is in an unilluminated state.

As shown in FIG. 2B, the pull tab 300, in the second position, may be disposed such that a proximal end 304 of the pull tab slot 302 is disposed proximate the pull tab stop 145. Accordingly, when the pull tab is moved from the first position to the second position, the pull tab stop 145 may be configured to retain the pull tab 300 within the housing of the illumination device, as the pull tab stop 145 is configured to contact the proximal end 304 of the pull tab slot 302 in the second position and prohibit the pull tab from further movement in that direction. In addition, some embodiments may include a pull tab 300 configured to advantageously provide for ease of removal from a speculum cavity 508. For example, as noted above when the proximal end 304 of the pull tab slot 302 is disposed proximate the pull tab stop 145, the pull tab may be prohibited from further movement along the longitudinal axis, such as the illumination axis I. As such, when tension is applied to the pull tab 300 along the longitudinal axis in an attempt to bias the pull tab from the first position to the second position, the pull tab stop 145 may be configured to retain the pull tab. Specifically, the pull tab stop 145 may extend along a direction orthogonal to the longitudinal axis of the pull tab and/or the longitudinal axis along which the pull tab travels between the two positions, such as illumination axis I. As such, the pull tab stop may be configured to transmit the tension such that the illumination device is moved along a direction parallel to the longitudinal axis of the pull tab, thereby assisting in the removal of the illumination device from the speculum cavity 508. For example, the pull tab may be pulled from the first position to the second position. When the pull tab reaches the second position, a user may continue to pull on the pull tab, which may cause the pull tab stop and the pull tab to contact one another. When a user continues to pull on the pull tab when the pull tab stop is in contact with the pull tab proximate the proximal end of the pull tab slot, the tension applied to the pull tab may cause the user to remove the illumination device from the speculum cavity.

Figure 7A:
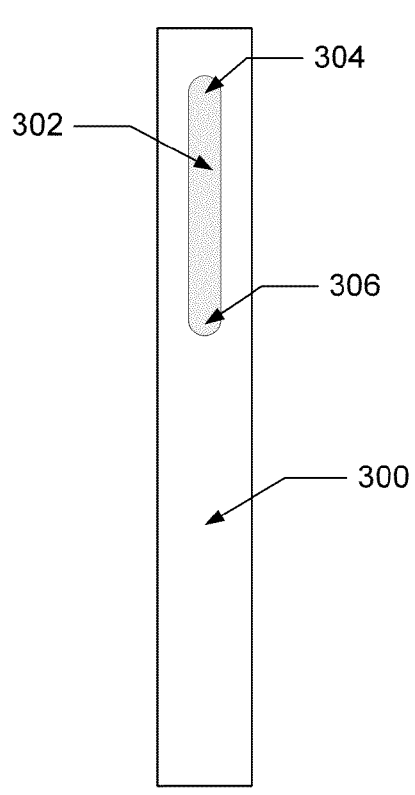
FIG. 7A illustrates a pull tab according to an example embodiment.
Figure 7B:
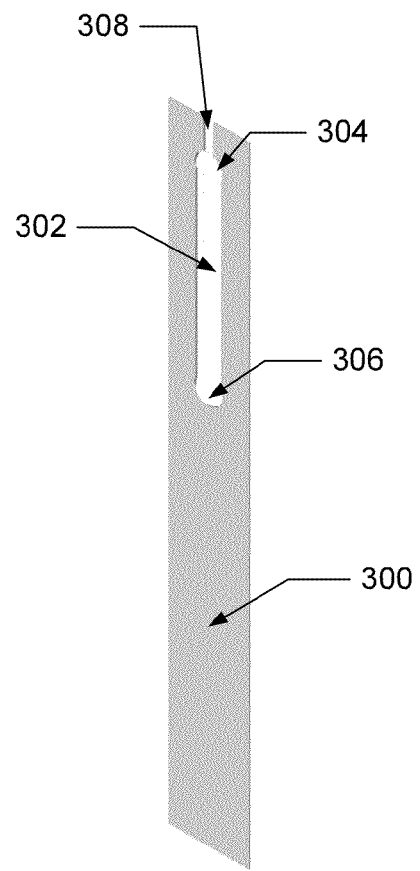
FIG. 7B illustrates a pull tab according to an example embodiment.

In another embodiment, as shown in FIG. 7B, the pull tab 300 may include a proximal end slit 308 disposed proximate the proximal end 304 of the pull tab slot 302. Accordingly, embodiments provided herein may be configured to provide a pull tab for an illumination device configured to move between a first position and a second position. As such, the pull tab 300 may be positioned to interrupt an electrical circuit in a first position such that the illumination device 10 is in an unilluminated state. In a second position, the pull tab 300 may be positioned so as to complete an electrical circuit such that the illumination device is in an illuminated state, as described in greater detail herein. Further, in some embodiments, the pull tab 300 may be configured to be removed from the illumination device 10 while the illumination device is disposed within the speculum cavity 508. According to some embodiments, the pull tab 300 may define a proximal end slit 308 disposed proximate the proximal end 304. The proximal end slit 308 may extend from the pull tab slot 302 to a peripheral edge of the pull tab 300. In some embodiments, the proximal end slit 308 may define a width that is narrower than a diameter of the pull tab stop 145. The proximal end slit 308 may be configured to allow the pull tab stop 145 to pass from the proximal end 304 of the pull tab slot 302, through the proximal end slit 308, and past a peripheral edge of the pull tab 300. As such, the pull tab 300 may be configured to be removed from the illumination device 10 while the illumination device remains within the speculum cavity 508.

In addition, when the pull tab 300 is disposed in the second position, the electrical circuit is completed (e.g., the pull tab is out of the way) such that the illumination device is in an illuminated state. Accordingly, when the pull tab 300 is disposed in the second position, the electrical circuit energizes the illumination source 200 so as to provide illumination. For example, when the pull tab is moved from the first position to the second position, the pull tab may be removed from a position between two batteries, thereby allowing the two batteries to contact one another. When the two batteries contact one another, an electrical circuit is completed so as to provide the illumination source with electrical power and thereby provide illumination. In some embodiments, the at least one battery may be configured to provide electrical power to the illumination source for illumination for at least 10 minutes. As mentioned herein, the pull tab 300 may be configured to move between the first and second position. As such, when the pull tab 300 is disposed in the second position (i.e., the electrical circuit energizes the illumination source), the pull tab may be moved from a second position to a first position, thereby interrupting the electrical circuit, such that the illumination device 10 changes from an illuminated state to an unilluminated state.

Figure 13:
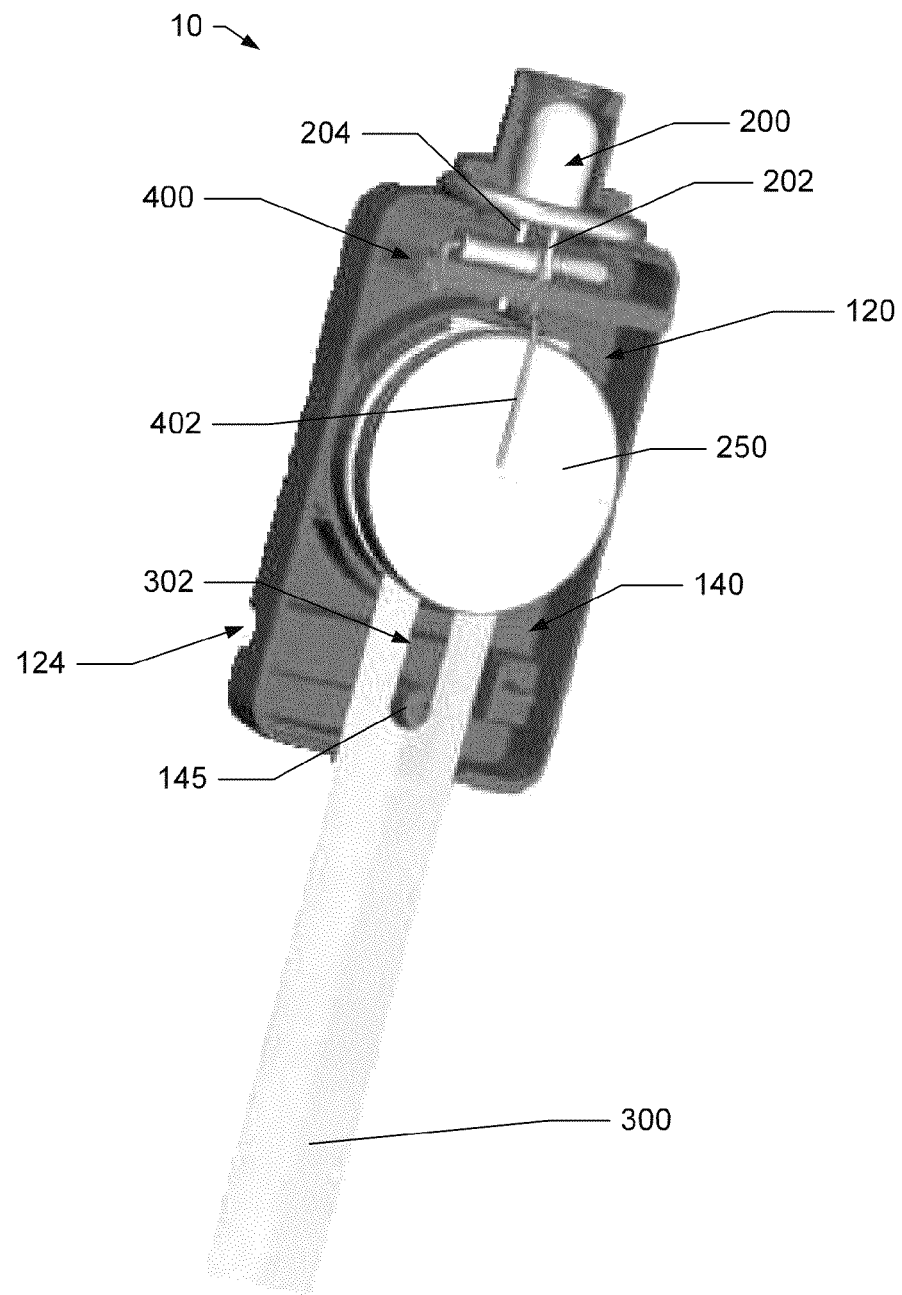
FIG. 13 illustrates a perspective view of an illumination device with various parts removed for clarity according to an example embodiment.

Turning to FIG. 13, according to some embodiments, the illumination device 10 may further include a current regulator 400, such as a circuit board including at least one resistor. In some embodiments where an illumination device 10 includes a current regulator 400, the first and second electrical contacts 202, 204 may be disposed such that an electrical connection is maintained between the current regulator 400 and the electrical contacts 202, 204 regardless of the position of the pull tab 300. In some embodiments, the electrical contacts 202, 204 may be disposed such that at least one electrical contact 202, 204 maintains an electrical connection with the current regulator 400. As shown in FIG. 13, a first electrical contact 202 may be disposed to maintain an electrical connection between the current regulator 400 and the electrical contact 202. The current regulator 400 may include at least one current regulator contact 402. As shown in FIG. 13, the current regulator contact 402 may be disposed to maintain an electrical connection between the current regulator 400 and the at least one battery 250. Accordingly, the current regulator 400 may define at least a portion of the electrical circuit between the at least one battery 250 and the illumination source 200. Embodiments herein that include such a current regulator may advantageously provide for more consistent illumination over a period of time. For example, an illumination device with a current regulator may be configured to prevent the brightness level of the illumination source from dropping off a few minutes after electrical power is provided to the illumination source. As a result, illumination from the illumination source is more consistent when an electrical circuit is completed to provide electrical power to the illumination source. Further, for embodiments having a single battery, a voltage booster (not shown) may optionally be included in the electrical circuit to advantageously provide for sufficient illumination.

FIGS. 9-12 show a speculum 500 that is configured to receive an illumination device 10 therein for illuminating a speculum and/or a patient during a physical exam. The speculum 500 may comprise a first blade 502 and a second blade 504. In addition, the speculum 500 may include a handle 506 configured to be gripped by a user during a physical examination. In some embodiments, the handle 506 and the second blade 504 may be integrally formed as a unitary member. In addition, the speculum 500 may include a light pipe 510. Further example speculums configured to receive an illumination device therein are discussed in commonly-assigned U.S. Pat. No. 8,157,728, dated Apr. 17, 2012, titled "VAGINAL SPECULUM," which is hereby incorporated by reference in its entirety.

Figure 10:
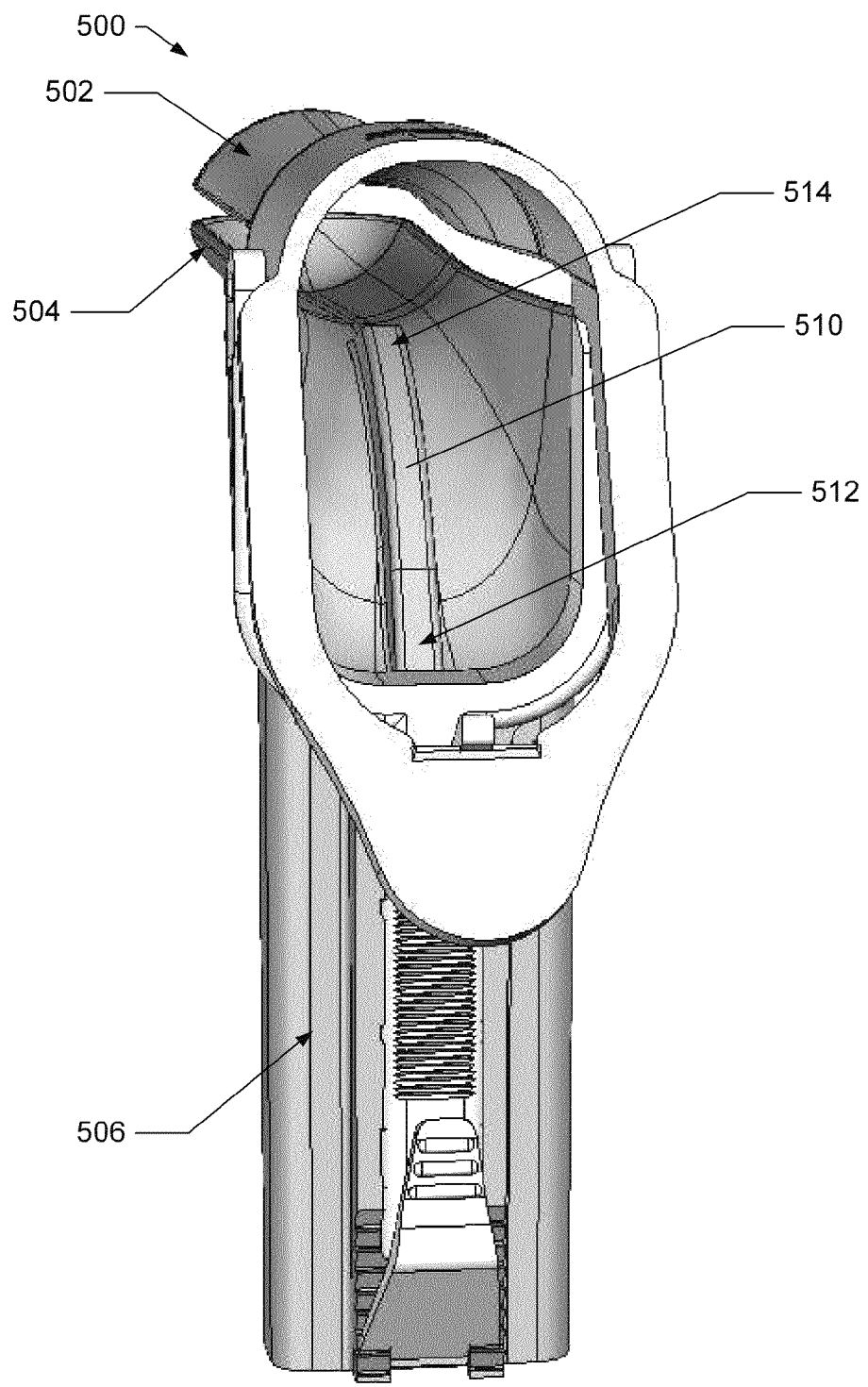
FIG. 10 illustrates a perspective rear view of a speculum according to an example embodiment.

In some embodiments, the light pipe 510 may be integrally formed with the second blade 504 and/or the handle 506 of the speculum. As shown in FIG. 10, the light pipe 510 may define a proximal end 512 and a distal end 514. In some embodiments, the proximal end 512 of the light pipe 510 may be disposed proximate the handle 506, and the distal end 514 of the light pipe 510 may be disposed proximate a point on the interior surface of the second blade 504. Accordingly, embodiments herein may advantageously provide for the illumination of a speculum and/or a patient by manipulating illumination provided by an illumination device disposed in one portion of the speculum to another portion of the speculum. Specifically, the light pipe may be configured to manipulate the illumination provided by the illumination device in the speculum cavity 508 such that the light is transmitted to and/or illuminates the distal end 514 of the light pipe 510. As such, the light pipe 510 may be configured to direct illumination within a speculum and/or toward a patient during a physical exam along a direction that is disposed at an angle to an illumination axis I defined by the illumination source and illumination device (shown in FIGS. 1 and 9). Specifically, the housing of the illumination device and the illumination source may define an illumination axis I that is parallel to the longitudinal axis of the speculum cavity when inserted therein. Accordingly, the light pipe may be configured to direct the illumination along an axis T that is tangential to the light pipe proximate the distal end 514 of the light pipe.

In some embodiments, the speculum 500 may be constructed from a transparent material. As such, the light pipe 510, the first blade 502 and/or the second blade 504 may be constructed from a transparent material, such as a plastic. In some embodiments, the speculum 500 may be constructed from a transparent material that is also refractive. As such, when illumination is provided to the light pipe via the illumination device, the light pipe, first blade, and/or second blade may be configured to amplify and/or concentrate the illumination towards a desired direction.

Embodiments herein may advantageously provide for increased illumination for a speculum for use during a physical exam of a patient. Further, some embodiments may advantageously provide for illumination of a speculum and/or patient that is substantially consistent in brightness. In some embodiments, an illumination device may be configured to be easily inserted within a speculum. In addition, the illumination device may be configured to advantageously provide for easy removal from a speculum cavity by providing a tapered portion to grasp for removal when the illumination device is disposed within the speculum cavity. Further, the illumination device may include a pull tab that may be used to activate the illumination device and/or provide for easy removal of the illumination device from a speculum cavity by providing a portion to pull upon when the illumination device is in place within the speculum cavity.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed. Although specific terms are employed herein, they are used in a generic and descriptive sense only and not for purposes of limitation.

That which is claimed:

1. An illumination device for a speculum comprising:
a housing comprising:
  a first housing part; and
  a second housing part,
    wherein the first housing part and the second housing part define a cavity therebetween;
an illumination source disposed within the housing;
a plurality of batteries disposed within the cavity of the housing configured to energize an electric circuit for providing power to the illumination source; and
a pull tab partially disposed within the cavity of the housing and configured to be moved between a first and second position,
wherein in the first position, the pull tab is disposed between at least two adjacent batteries to preclude electrical contact between the two batteries and interrupt the electric circuit such that the illumination device is in an unilluminated state, and wherein in the second position, the pull tab is positioned to allow electrical contact between the two batteries to complete the electric circuit such that the illumination device is in an illuminated state, and
wherein the pull tab defines a pull tab slot therethrough, wherein the pull tab slot is configured to retain the pull tab at least partially within the cavity in the second position.

2. An illumination device according to claim 1 further comprising a current regulator device disposed within the housing and configured to regulate the power to the illumination source.

3. An illumination device according to claim 1 further comprising a voltage boost regulator disposed within the housing and configured to regulate the voltage to provide sufficient illumination.

4. An illumination device according to claim 1, wherein the housing further defines a pull tab stop, the pull tab stop being configured to engage an end of the pull tab.

5. An illumination device according to claim 4, wherein an inner surface of the housing defines the pull tab stop.

6. An illumination device according to claim 4, wherein a first inner surface of the first housing part defines a first portion of the pull tab stop and a second inner surface of the second housing part defines a second portion of the pull tab stop.

7. An illumination device according to claim 4, wherein the pull tab stop extends along an axis orthogonal to a longitudinal axis of the pull tab.

8. An illumination device according to claim 1, wherein the pull tab is configured to move in a direction substantially parallel to a longitudinal axis of the illumination device.

9. An illumination device according to claim 1, wherein an outer surface of the housing defines a plurality of raised grooves configured to mate with reciprocal channels of a speculum cavity so as to facilitate alignment of the illumination device therein.

10. An illumination device according to claim 1, wherein the housing defines a first portion, a second portion and a third portion, wherein the illumination source is disposed proximate the first portion, and wherein the pull tab is disposed proximate the third portion.

11. An illumination device according to claim 10, wherein the second portion has a shape substantially corresponding to a shape of a battery.

12. An illumination device according to claim 1, further comprising at least one securing member configured to maintain engagement of the first housing part with the second housing part.

13. An illumination device according to claim 12, wherein the at least one securing member is a wire clip member, wherein the wire clip member is configured to bias the housing parts together.

14. An illumination device according to claim 12, wherein the at least one securing member is an elastomeric material, wherein the elastomeric material is configured to bias the housing parts together.

15. A system comprising:
   a speculum comprising:
      a handle defining a handle cavity therein; and
      at least two blades, wherein a second blade is coupled to the handle; and
   an illumination device comprising:
      a housing comprising:
         a first housing part; and
         a second housing part,
            wherein the first housing part and the second housing part define a housing cavity therebetween;
      an illumination source disposed within the housing;
      a battery disposed within the housing cavity of the housing configured to energize an electric circuit for providing power to the illumination source; and
      a pull tab partially disposed within the housing cavity and configured to be moved between a first and second position,
         wherein in the first position, the pull tab is positioned to interrupt the electric circuit such that the illumination device is in an unilluminated state, and wherein in the second position, the pull tab is positioned to allow the electric circuit to be complete such that the illumination device is in an illuminated state,
      wherein the pull tab defines a pull tab slot therethrough, wherein the pull tab slot is configured to retain the pull tab at least partially within the housing cavity in the second position.

16. A system according to claim 15, wherein the speculum further comprises a light pipe configured to illuminate the speculum, wherein the light pipe extends from a proximal end disposed proximate the handle to a distal end disposed proximate the second blade.

17. A system according to claim 16, wherein the illumination device further comprises a plurality of batteries disposed within the housing cavity, wherein in the first position the pull tab is disposed between at least two adjacent batteries to preclude electrical contact between the two batteries, and wherein in the second position, the pull tab is positioned to allow electrical contact between the two batteries.

18. A system according to claim 15, wherein the handle cavity is configured to receive the illumination device therein, and wherein the illumination source is configured to illuminate the proximal end of the light pipe thereby illuminating the speculum.

19. A system according to claim 15, wherein the housing further defines a pull tab stop, the pull tab stop being configured to engage an end of the pull tab.

20. A system according to claim 19, wherein an inner surface of the housing defines the pull tab stop.

21. A system according to claim 19, wherein the illumination device is configured to be removed from a handle cavity of the speculum when tension is applied to the pull tab after the pull tab stop is engaged with an end of the pull tab slot.

* * * * *